United States Patent [19]

Bellina

[11] Patent Number: 5,069,709

[45] Date of Patent: Dec. 3, 1991

[54] HERBICIDAL THIADIAZOLO PYRIMIDINES

[75] Inventor: Russell F. Bellina, Wilmington, Del.

[73] Assignee: E. I. Du Pont de Nemours and Company, Wilmington, Del.

[21] Appl. No.: 492,575

[22] Filed: Mar. 8, 1990

[51] Int. Cl.$^5$ .................... A01N 43/90; C07D 513/04
[52] U.S. Cl. .......................................... 71/90; 544/255
[58] Field of Search .......................... 71/90; 544/255

[56] References Cited

U.S. PATENT DOCUMENTS 4,872,901 10/1989 Aoki ........................................ 71/90

FOREIGN PATENT DOCUMENTS

| 239064 | 9/1987 | European Pat. Off. . |
| 61-104532 | 11/1987 | Japan . |
| 62-287088 | 5/1989 | Japan . |
| 63-20807 | 7/1989 | Japan . |
| 63-65049 | 9/1989 | Japan . |

OTHER PUBLICATIONS

Aoki et al., Chemical Abstracts, vol. 107, entry 176057r (1987).
Okada et al., Chemical Abstracts, vol. 108, entry 94586u (1988).
Hagiwara et al., Chemical Abstracts, vol. 109, entry 73484q (1988).
Okajima et al., Chemical Abstracts, vol. 110, entry 212813g (1989).
Kimura et al., Chemical Abstracts, vol. 112, entry 35901c (1990).
Kimura et al., Chemical Abstracts, vol. 112, entry 179010j (1990).
Kimura et al., Chemical Abstracts, vol. 112, entry 179016r (1990).

*Primary Examiner*—John M. Ford

[57] ABSTRACT

This invention relates to certain herbicidal thiadiazoloazines, agriculturally suitable compositions thereof and a method for their use as a general or selective preemergent or postemergent herbicide or as a plant growth regulant.

15 Claims, No Drawings

HERBICIDAL THIADIAZOLO PYRIMIDINES

BACKGROUND OF THE INVENTION

This invention relates to certain herbicidal thiadiazoloazines, agriculturally suitable compositions thereof and a method for their use as a general or selective preemergent or postemergent herbicide or as a plant growth regulant.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. There are many products commercially available for these purposes, but the search continues for products which are most effective, less costly and environmentally safe.

U.S. Pat. No. 4,872,901 discloses herbicidal thiadiazoloazines of the formula

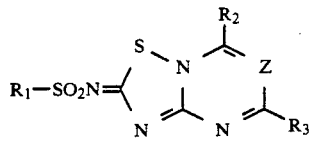

wherein
$R_1$ is a pyrazolyl group which may be substituted;
$R_2$ and $R_3$ are respectively lower alkyl or lower alkoxy; and
Z is CH or N.

EP-A-239,064 discloses herbicidal thiadiazoloazines of the formula

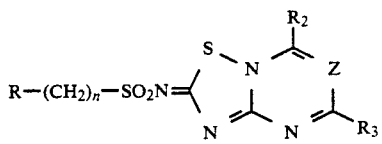

wherein
R is optionally substituted phenyl;
$R_2$ and $R_3$ are independently lower alkyl or lower alkoxy;
Z is CH or N; and
n is 0 or 1.

Japanese Patent Application 62[1987]-287088 and Japanese Patent Application 63[1988]-2080 disclose herbicidal thiadiazoloazines of the formula

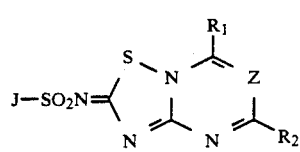

wherein

-continued

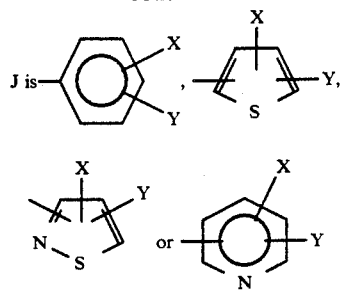

wherein
X is H, halogen, alkyl, haloalkyl, alkoxy, haloalkoxy, alkoxyalkyl, haloalkoxyalkyl, $C(O)N(R_3)R_4$, $C(O)OR_5$;
Y is H, halogen, alkyl or haloalkyl;
$R_1$ and $R_2$ are independently alkyl, alkoxy or Cl; and
Z is CH or N.

Japanese Patent Application 63[1988]-65049 discloses herbicidal bisdifluoromethoxy thiadiazoloazines of the formula

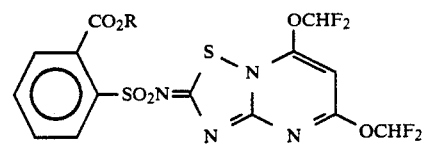

wherein
R is alkyl.

Japanese Patent Application 61[1986]-104,532 discloses herbicidal thiadiazoloazines of the formula

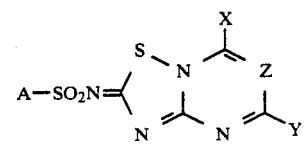

wherein
A is lower alkyl, lower alkoxycarbonyl, phenyl with or without a halogen substituent, 5- or 6-membered aromatic heterocyclic ring containing an oxygen, sulfur and/or nitrogen atom, aralkyl group;
Z is CH or N; and
X and Y are independently halogen, lower alkyl or lower alkoxy.

SUMMARY OF THE INVENTION

The invention comprises novel compounds of Formula I,

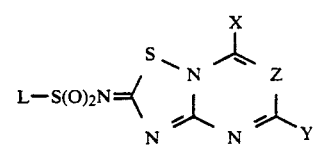

wherein L is

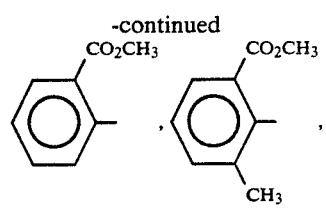

L-1, L-2

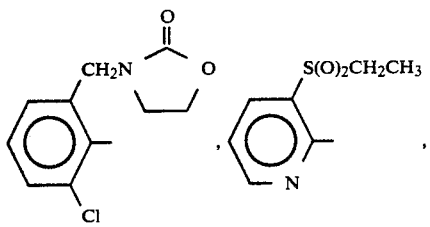

L-3, L-4

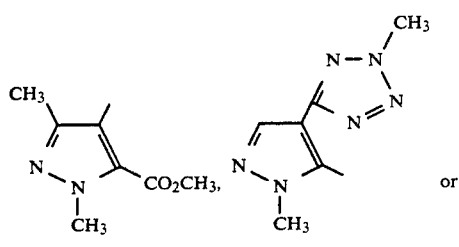

L-5, L-6 or

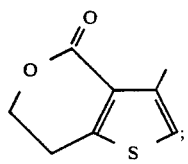

L-7

X and Y are independently $C_1$-$C_2$ alkyl, $C_1$-$C_2$ alkoxy, $C_1$-$C_2$ haloalkoxy, $NHCH_3$ or $N(CH_3)_2$; and Z is CH or N;

and their agriculturally suitable salts provided that 1) when X and/or Y is $C_1$ haloalkoxy, then Z is CH; and 2) when L is L-1 or L-2, then at least one of X and Y is $NHCH_3$ or $N(CH_3)_2$.

In the above definitions, the term "alkyl", used either alone or in compound words such as "haloalkyl", denotes methyl or ethyl. Similarly alkoxy denotes methoxy or ethoxy.

The term "halogen", either alone or in compound words such as "haloalkyl", denotes fluorine, chlorine, bromine or iodine. Further, when used in compound words such as "haloalkyl" said alkyl may be partially halogenated or fully substituted with halogen atoms and said halogen atoms may be the same or different. Examples of haloalkoxy include $OCF_2H$ and $OCH_2CF_3$.

The total number of carbon atoms in a substituent group is indicated by the $C_i$-$C_j$ prefix where i and j are numbers 1 to 2. For example, $C_1$-$C_2$ alkyl would designate methyl through ethyl.

Compounds of the invention preferred for reasons of expected increased ease of synthesis and/or greater herbicidal efficacy are:

1. Compounds of Formula I where if one of X or Y is $NHCH_3$ or $N(CH_3)_2$, then the other of X and Y is other than $NHCH_3$ or $N(CH_3)_2$.

2. Compounds of Preferred 1 where X and Y are independently $C_1$-$C_2$ alkyl, $C_1$-$C_2$ alkoxy, $OCF_2H$ or $OCH_2CF_3$, or one of X and Y can be $NHCH_3$ or $N(CH_3)_2$.

3. Compounds of Preferred 2 where Z is N.

4. Compounds of Preferred 2 where Z is CH.

5. Compounds of Preferred 4 where X and Y are independently $CH_3$ or $OCH_3$.

Compounds of the invention specifically preferred for reasons of expected ease of synthesis and/or greatest herbicidal efficacy and/or crop safety are:

N-(5,7-dimethoxy-2H-[1,2,4]thiadiazolo[2,3-a]pyrimidin-2-ylidene)-3-(ethylsulfonyl)-2-pyridinesulfonamide (Formula I, L is L-4, X and Y are $OCH_3$, and Z is CH)

N-(5,7-dimethoxy-2H-[1,2,4]thiadiazolo[2,3-a]pyrimidin-2-ylidene)-1-methyl-4-(2-methyl-2H-tetrazol-5-yl)-1H-pyrazole -5-sulfonamide (Formula I, L is L-6, X and Y are $OCH_3$, and Z is CH)

The present invention also includes agriculturally suitable compositions of the compounds of the invention and a method of using the compounds of the invention as preemergent and/or postemergent herbicides or plant growth regulants. Some of the compounds of the invention are expected to demonstrate useful safety to crops such as wheat, rice, corn, oilseed rape, sugar beets, tomatoes and potatoes.

DETAILED DESCRIPTION OF THE INVENTION

Synthesis

Compounds of the Formula I are preparable as outlined in Equation 1.

Equation 1:

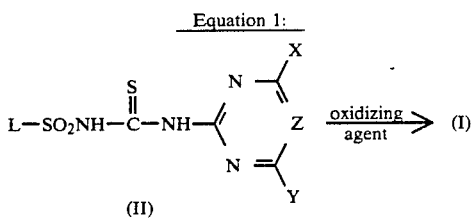

where L, X, Y and Z are as previously defined.

Equation 1 illustrates a preferred method in which sulfonylthioureas represented by general Formula II can be reacted with oxidizing agents such as chlorine, bromine, N-chlorosuccinimide or N-bromosuccinimide, and a base such as pyridine or triethylamine may be used as an acid scavenger.

The reaction is best carried out at about −5° C. or below for about 0.5 to 1 hours in an inert solvent such as methanol, benzene or pyridine under an inert atmosphere.

The sulfonylthioureas represented by Formula II are prepared by the procedures outlined in Equation 2.

Equation 2:

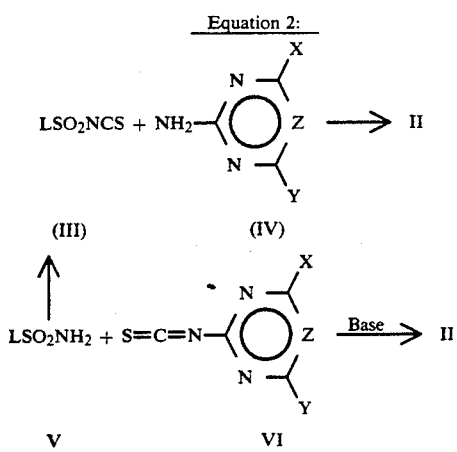

where L, X, Y and Z are as previously described.

The reaction of Equation 2a is carried out by reacting the sulfonyl isothiocyanate III with heterocyclic amine IV in an inert solvent such as acetonitrile at about 10° C. to 80° C. under an inert atmosphere as described in the art, e.g., U.S. Pat. No. 4,127,405, or modifications thereof.

The sulfonyl isothiocyanates III are known in the art and are prepared from the corresponding sulfonamides V by the reaction with carbon disulfide and potassium hydroxide followed by treatment of the resulting dipotassium salt with phosgene. Such a procedure is described in Arch. Pharm. 299, 174 (1966).

Alternatively compounds of Formula II are prepared according to Equation 2b. The sulfonamide V is reacted under an inert atmosphere with an isothiocyanate of Formula VI in the presence of a base such as potassium carbonate and an inert solvent such as methanol, acetonitrile or acetone at a temperature about 0–50° C. for about 2–14 hours.

Sulfonamides V and isothiocyanates VI are known in the art.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt of the resin and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following two Examples.

EXAMPLE 1

1-Methyl-4-(2-methyl-2H-tetrazol-5-yl) -N-[(4,6-dimethoxy-2-pyrimidinyl)amino]thiocarbonyl]-1H-pyrazole-5-sulfonamide A mixture of 1-methyl-4-(2-methyl-2H-tetrazol -5-yl)-1H-pyrazole-5-sulfonamide (2.0 mmol) and 4,6-dimethoxy-2-isothiocyanatopyrimidine (2.0 mmol), potassium carbonate (2.0 mmol) and acetone (20 ml) was mechanically stirred at room temperature for 14 hours and 3 hours at reflux. A solid was filtered off and suspended in 10 ml of water and acidified with hydrochloric acid. The resulting precipitate was collected, washed with water and dried to yield 0.55 g of the title compound as a yellow solid, melting point 188–190° C.

EXAMPLE 2

N-(5,7-dimethoxy-2H-[1,2,4]thiadiazolo[2,3-a]pyrimidin-2-ylidene)-1-methyl-4-(2-methyl -2H-tetrazol-5-yl)-1H-pyrazole-5-sulfonamide 1-methyl-4-(2-methyl-2H-tetrazol-5-yl)-N-[(4,6-dimethoxy-2-pyrimidinyl)amino]thiocarbonyl]-1H -pyrazole-5-sulfonamide (0.5 mmol), was suspended in methanol (10 ml) and N-bromosuccinimide (0.55 mmol) was added at −5° C. The mixture was stirred at the same temperature for one-half hour to complete the reaction. The resulting solid was collected by filtration and washed with methanol to provide 0.2 g of the title compound as a white solid, melting point 182–183° C.

Using the techniques described in Equation 1 and 2 and Examples 1 and 2 or simple modifications thereof, the following thiadiazoloazines in Table 1 can be made by one skilled in the art.

TABLE 1

| L | X | Y | Z |
|---|---|---|---|
| L-1 | NHCH3 | OCH3 | CH |
| L-1 | NHCH3 | CH3 | CH |
| L-1 | NHCH3 | OCH2CF3 | CH |
| L-1 | NHCH3 | OCF2H | CH |
| L-1 | OCH3 | NHCH3 | CH |
| L-1 | CH3 | NHCH3 | CH |
| L-1 | OCH2CF3 | NHCH3 | CH |
| L-1 | OCF2H | NHCH3 | CH |
| L-1 | N(CH3)2 | OCH3 | CH |
| L-1 | N(CH3)2 | CH3 | CH |
| L-1 | N(CH3)2 | OCH2CF3 | CH |
| L-1 | N(CH3)2 | OCF2H | CH |
| L-1 | OCH3 | N(CH3)2 | CH |
| L-1 | CH3 | N(CH3)2 | CH |
| L-1 | OCH2CF3 | N(CH3)2 | CH |
| L-1 | OCF2H | N(CH3)2 | CH |
| L-1 | NHCH3 | OCH2CH3 | CH |
| L-1 | OCH2CH3 | NHCH3 | CH |
| L-1 | N(CH3)2 | OCH2CH3 | CH |
| L-1 | OCH2CH3 | N(CH3)2 | CH |
| L-1 | NHCH3 | OCH3 | N |
| L-1 | NHCH3 | CH3 | N |
| L-1 | NHCH3 | OCH2CF3 | N |
| L-1 | NHCH3 | OCF2H | N |

TABLE 1-continued

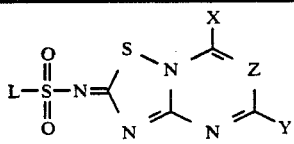

| L | X | Y | Z |
|---|---|---|---|
| L-1 | OCH₃ | NHCH₃ | N |
| L-1 | CH₃ | NHCH₃ | N |
| L-1 | OCH₂CF₃ | NHCH₃ | N |
| L-1 | OCF₂H | NHCH₃ | N |
| L-1 | N(CH₃)₂ | OCH₃ | N |
| L-1 | N(CH₃)₂ | CH₃ | N |
| L-1 | N(CH₃)₂ | OCH₂CF₃ | N |
| L-1 | N(CH₃)₂ | OCF₂H | N |
| L-1 | OCH₃ | N(CH₃)₂ | N |
| L-1 | CH₃ | N(CH₃)₂ | N |
| L-1 | OCH₂CF₃ | N(CH₃)₂ | N |
| L-1 | OCF₂H | N(CH₃)₂ | N |
| L-1 | NHCH₃ | OCH₂CH₃ | N |
| L-1 | OCH₂CH₃ | NHCH₃ | N |
| L-1 | N(CH₃)₂ | OCH₂CH₃ | N |
| L-1 | OCH₂CH₃ | N(CH₃)₂ | N |
| L-2 | NHCH₃ | OCH₃ | CH |
| L-2 | NHCH₃ | CH₃ | CH |
| L-2 | NHCH₃ | OCH₂CF₃ | CH |
| L-2 | NHCH₃ | OCF₂H | CH |
| L-2 | OCH₃ | NHCH₃ | CH |
| L-2 | CH₃ | NHCH₃ | CH |
| L-2 | OCH₂CF₃ | NHCH₃ | CH |
| L-2 | OCF₂H | NHCH₃ | CH |
| L-2 | N(CH₃)₂ | OCH₃ | CH |
| L-2 | N(CH₃)₂ | CH₃ | CH |
| L-2 | N(CH₃)₂ | OCH₂CF₃ | CH |
| L-2 | N(CH₃)₂ | OCF₂H | CH |
| L-2 | OCH₃ | N(CH₃)₂ | CH |
| L-2 | CH₃ | N(CH₃)₂ | CH |
| L-2 | OCH₂CF₃ | N(CH₃)₂ | CH |
| L-2 | OCF₂H | N(CH₃)₂ | CH |
| L-2 | NHCH₃ | OCH₂CH₃ | CH |
| L-2 | OCH₂CH₃ | NHCH₃ | CH |
| L-2 | N(CH₃)₂ | OCH₂CH₃ | CH |
| L-2 | OCH₂CH₃ | N(CH₃)₂ | CH |
| L-2 | NHCH₃ | OCH₃ | N |
| L-2 | NHCH₃ | CH₃ | N |
| L-2 | NHCH₃ | OCH₂CF₃ | N |
| L-2 | NHCH₃ | OCF₂H | N |
| L-2 | OCH₃ | NHCH₃ | N |
| L-2 | CH₃ | NHCH₃ | N |
| L-2 | OCH₂CF₃ | NHCH₃ | N |
| L-2 | OCF₂H | NHCH₃ | N |
| L-2 | N(CH₃)₂ | OCH₃ | N |
| L-2 | N(CH₃)₂ | CH₃ | N |
| L-2 | N(CH₃)₂ | OCH₂CF₃ | N |
| L-2 | N(CH₃)₂ | OCF₂H | N |
| L-2 | OCH₃ | N(CH₃)₂ | N |
| L-2 | CH₃ | N(CH₃)₂ | N |
| L-2 | OCH₂CF₃ | N(CH₃)₂ | N |
| L-2 | OCF₂H | N(CH₃)₂ | N |
| L-2 | NHCH₃ | OCH₂CH₃ | N |
| L-2 | OCH₂CH₃ | NHCH₃ | N |
| L-2 | N(CH₃)₂ | OCH₂CH₃ | N |
| L-2 | OCH₂CH₃ | N(CH₃)₂ | N |
| L-3 | NHCH₃ | OCH₃ | CH |
| L-3 | NHCH₃ | CH₃ | CH |
| L-3 | NHCH₃ | OCH₂CF₃ | CH |
| L-3 | NHCH₃ | OCF₂H | CH |
| L-3 | OCH₃ | NHCH₃ | CH |
| L-3 | CH₃ | NHCH₃ | CH |
| L-3 | OCH₂CF₃ | NHCH₃ | CH |
| L-3 | OCF₂H | NHCH₃ | CH |
| L-3 | N(CH₃)₂ | OCH₃ | CH |
| L-3 | N(CH₃)₂ | CH₃ | CH |
| L-3 | N(CH₃)₂ | OCH₂CF₃ | CH |
| L-3 | N(CH₃)₂ | OCF₂H | CH |
| L-3 | OCH₃ | N(CH₃)₂ | CH |
| L-3 | CH₃ | N(CH₃)₂ | CH |
| L-3 | OCH₂CF₃ | N(CH₃)₂ | CH |
| L-3 | OCF₂H | N(CH₃)₂ | CH |
| L-3 | OCH₃ | OCH₃ | CH |

TABLE 1-continued

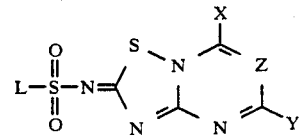

| L | X | Y | Z |
|---|---|---|---|
| L-3 | OCH₃ | CH₃ | CH |
| L-3 | CH₃ | OCH₃ | CH |
| L-3 | CH₃ | CH₃ | CH |
| L-3 | CH₃ | Cl | CH |
| L-3 | Cl | CH₃ | CH |
| L-3 | Cl | OCH₃ | CH |
| L-3 | OCH₃ | Cl | CH |
| L-3 | OCH₃ | OCH₃ | N |
| L-3 | OCH₃ | CH₃ | N |
| L-3 | CH₃ | OCH₃ | N |
| L-3 | CH₃ | CH₃ | N |
| L-3 | CH₃ | Cl | N |
| L-3 | Cl | CH₃ | N |
| L-3 | Cl | OCH₃ | N |
| L-3 | OCH₃ | Cl | N |
| L-3 | NHCH₃ | OCH₃ | N |
| L-3 | NHCH₃ | CH₃ | N |
| L-3 | NHCH₃ | OCH₂CF₃ | N |
| L-3 | NHCH₃ | OCF₂H | N |
| L-3 | OCH₃ | NHCH₃ | N |
| L-3 | CH₃ | NHCH₃ | N |
| L-3 | OCH₂CF₃ | NHCH₃ | N |
| L-3 | OCF₂H | NHCH₃ | N |
| L-3 | N(CH₃)₂ | OCH₃ | N |
| L-3 | N(CH₃)₂ | CH₃ | N |
| L-3 | N(CH₃)₂ | OCH₂CF₃ | N |
| L-3 | N(CH₃)₂ | OCF₂H | N |
| L-3 | OCH₃ | N(CH₃)₂ | N |
| L-3 | CH₃ | N(CH₃)₂ | N |
| L-3 | OCH₂CF₃ | N(CH₃)₂ | N |
| L-3 | OCF₂H | N(CH₃)₂ | N |
| L-4 | NHCH₃ | OCH₃ | CH |
| L-4 | NHCH₃ | CH₃ | CH |
| L-4 | NHCH₃ | OCH₂CF₃ | CH |
| L-4 | NHCH₃ | OCF₂H | CH |
| L-4 | OCH₃ | NHCH₃ | CH |
| L-4 | CH₃ | NHCH₃ | CH |
| L-4 | OCH₂CF₃ | NHCH₃ | CH |
| L-4 | OCF₂H | NHCH₃ | CH |
| L-4 | N(CH₃)₂ | OCH₃ | CH |
| L-4 | N(CH₃)₂ | CH₃ | CH |
| L-4 | N(CH₃)₂ | OCH₂CF₃ | CH |
| L-4 | N(CH₃)₂ | OCF₂H | CH |
| L-4 | OCH₃ | N(CH₃)₂ | CH |
| L-4 | CH₃ | N(CH₃)₂ | CH |
| L-4 | OCH₂CF₃ | N(CH₃)₂ | CH |
| L-4 | OCF₂H | N(CH₃)₂ | CH |
| L-4 | OCH₃ | OCH₃ | CH |
| L-4 | OCH₃ | CH₃ | CH |
| L-4 | CH₃ | OCH₃ | CH |
| L-4 | CH₃ | CH₃ | CH |
| L-4 | CH₃ | Cl | CH |
| L-4 | Cl | CH₃ | CH |
| L-4 | Cl | OCH₃ | CH |
| L-4 | OCH₃ | Cl | CH |
| L-4 | OCH₃ | OCH₃ | N |
| L-4 | OCH₃ | CH₃ | N |
| L-4 | CH₃ | OCH₃ | N |
| L-4 | CH₃ | CH₃ | N |
| L-4 | CH₃ | Cl | N |
| L-4 | Cl | CH₃ | N |
| L-4 | Cl | OCH₃ | N |
| L-4 | OCH₃ | Cl | N |
| L-4 | NHCH₃ | OCH₃ | N |
| L-4 | NHCH₃ | CH₃ | N |
| L-4 | NHCH₃ | OCH₂CF₃ | N |
| L-4 | NHCH₃ | OCF₂H | N |
| L-4 | OCH₃ | NHCH₃ | N |
| L-4 | CH₃ | NHCH₃ | N |
| L-4 | OCH₂CF₃ | NHCH₃ | N |
| L-4 | OCF₂H | NHCH₃ | N |
| L-4 | N(CH₃)₂ | OCH₃ | N |
| L-4 | N(CH₃)₂ | CH₃ | N |

TABLE 1-continued

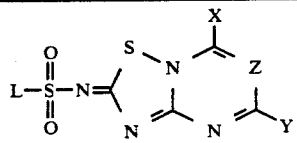

| L | X | Y | Z |
|---|---|---|---|
| L-4 | N(CH$_3$)$_2$ | OCH$_2$CF$_3$ | N |
| L-4 | N(CH$_3$)$_2$ | OCF$_2$H | N |
| L-4 | OCH$_3$ | N(CH$_3$)$_2$ | N |
| L-4 | CH$_3$ | N(CH$_3$)$_2$ | N |
| L-4 | OCH$_2$CF$_3$ | N(CH$_3$)$_2$ | N |
| L-4 | OCF$_2$H | N(CH$_3$)$_2$ | N |
| L-5 | NHCH$_3$ | OCH$_3$ | CH |
| L-5 | NHCH$_3$ | CH$_3$ | CH |
| L-5 | NHCH$_3$ | OCH$_2$CF$_3$ | CH |
| L-5 | NHCH$_3$ | OCF$_2$H | CH |
| L-5 | OCH$_3$ | NHCH$_3$ | CH |
| L-5 | CH$_3$ | NHCH$_3$ | CH |
| L-5 | OCH$_2$CF$_3$ | NHCH$_3$ | CH |
| L-5 | OCF$_2$H | NHCH$_3$ | CH |
| L-5 | N(CH$_3$)$_2$ | OCH$_3$ | CH |
| L-5 | N(CH$_3$)$_2$ | CH$_3$ | CH |
| L-5 | N(CH$_3$)$_2$ | OCH$_2$CF$_3$ | CH |
| L-5 | N(CH$_3$)$_2$ | OCF$_2$H | CH |
| L-5 | OCH$_3$ | N(CH$_3$)$_2$ | CH |
| L-5 | CH$_3$ | N(CH$_3$)$_2$ | CH |
| L-5 | OCH$_2$CF$_3$ | N(CH$_3$)$_2$ | CH |
| L-5 | OCF$_2$H | N(CH$_3$)$_2$ | CH |
| L-5 | OCH$_3$ | OCH$_3$ | CH |
| L-5 | OCH$_3$ | CH$_3$ | CH |
| L-5 | CH$_3$ | OCH$_3$ | CH |
| L-5 | CH$_3$ | CH$_3$ | CH |
| L-5 | CH$_3$ | Cl | CH |
| L-5 | Cl | CH$_3$ | CH |
| L-5 | Cl | OCH$_3$ | CH |
| L-5 | OCH$_3$ | Cl | CH |
| L-5 | OCH$_3$ | OCH$_3$ | N |
| L-5 | OCH$_3$ | CH$_3$ | N |
| L-5 | CH$_3$ | OCH$_3$ | N |
| L-5 | CH$_3$ | CH$_3$ | N |
| L-5 | CH$_3$ | Cl | N |
| L-5 | Cl | CH$_3$ | N |
| L-5 | Cl | OCH$_3$ | N |
| L-5 | OCH$_3$ | Cl | N |
| L-5 | NHCH$_3$ | OCH$_3$ | N |
| L-5 | NHCH$_3$ | CH$_3$ | N |
| L-5 | NHCH$_3$ | OCH$_2$CF$_3$ | N |
| L-5 | NHCH$_3$ | OCF$_2$H | N |
| L-5 | OCH$_3$ | NHCH$_3$ | N |
| L-5 | CH$_3$ | NHCH$_3$ | N |
| L-5 | OCH$_2$CF$_3$ | NHCH$_3$ | N |
| L-5 | OCF$_2$H | NHCH$_3$ | N |
| L-5 | N(CH$_3$)$_2$ | OCH$_3$ | N |
| L-5 | N(CH$_3$)$_2$ | CH$_3$ | N |
| L-5 | N(CH$_3$)$_2$ | OCH$_2$CF$_3$ | N |
| L-5 | N(CH$_3$)$_2$ | OCF$_2$H | N |
| L-5 | OCH$_3$ | N(CH$_3$)$_2$ | N |
| L-5 | CH$_3$ | N(CH$_3$)$_2$ | N |
| L-5 | OCH$_2$CF$_3$ | N(CH$_3$)$_2$ | N |
| L-5 | OCF$_2$H | N(CH$_3$)$_2$ | N |
| L-6 | NHCH$_3$ | OCH$_3$ | CH |
| L-6 | NHCH$_3$ | CH$_3$ | CH |
| L-6 | NHCH$_3$ | OCH$_2$CF$_3$ | CH |
| L-6 | NHCH$_3$ | OCF$_2$H | CH |
| L-6 | OCH$_3$ | NHCH$_3$ | CH |
| L-6 | CH$_3$ | NHCH$_3$ | CH |
| L-6 | OCH$_2$CF$_3$ | NHCH$_3$ | CH |
| L-6 | OCF$_2$H | NHCH$_3$ | CH |
| L-6 | N(CH$_3$)$_2$ | OCH$_3$ | CH |
| L-6 | N(CH$_3$)$_2$ | CH$_3$ | CH |
| L-6 | N(CH$_3$)$_2$ | OCH$_2$CF$_3$ | CH |
| L-6 | N(CH$_3$)$_2$ | OCF$_2$H | CH |
| L-6 | OCH$_3$ | N(CH$_3$)$_2$ | CH |
| L-6 | CH$_3$ | N(CH$_3$)$_2$ | CH |
| L-6 | OCH$_2$CF$_3$ | N(CH$_3$)$_2$ | CH |
| L-6 | OCF$_2$H | N(CH$_3$)$_2$ | CH |
| L-6 | OCH$_3$ | OCH$_3$ | CH |
| L-6 | OCH$_3$ | CH$_3$ | CH |
| L-6 | CH$_3$ | OCH$_3$ | CH |

TABLE 1-continued

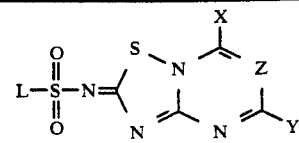

| L | X | Y | Z |
|---|---|---|---|
| L-6 | CH$_3$ | CH$_3$ | CH |
| L-6 | CH$_3$ | Cl | CH |
| L-6 | Cl | CH$_3$ | CH |
| L-6 | Cl | OCH$_3$ | CH |
| L-6 | OCH$_3$ | Cl | CH |
| L-6 | OCH$_3$ | OCH$_3$ | N |
| L-6 | OCH$_3$ | CH$_3$ | N |
| L-6 | CH$_3$ | OCH$_3$ | N |
| L-6 | CH$_3$ | CH$_3$ | N |
| L-6 | CH$_3$ | Cl | N |
| L-6 | Cl | CH$_3$ | N |
| L-6 | Cl | OCH$_3$ | N |
| L-6 | OCH$_3$ | Cl | N |
| L-6 | NHCH$_3$ | OCH$_3$ | N |
| L-6 | NHCH$_3$ | CH$_3$ | N |
| L-6 | NHCH$_3$ | OCH$_2$CF$_3$ | N |
| L-6 | NHCH$_3$ | OCF$_2$H | N |
| L-6 | OCH$_3$ | NHCH$_3$ | N |
| L-6 | CH$_3$ | NHCH$_3$ | N |
| L-6 | OCH$_2$CF$_3$ | NHCH$_3$ | N |
| L-6 | OCF$_2$H | NHCH$_3$ | N |
| L-6 | N(CH$_3$)$_2$ | OCH$_3$ | N |
| L-6 | N(CH$_3$)$_2$ | CH$_3$ | N |
| L-6 | N(CH$_3$)$_2$ | OCH$_2$CF$_3$ | N |
| L-6 | N(CH$_3$)$_2$ | OCF$_2$H | N |
| L-6 | OCH$_3$ | N(CH$_3$)$_2$ | N |
| L-6 | CH$_3$ | N(CH$_3$)$_2$ | N |
| L-6 | OCH$_2$CF$_3$ | N(CH$_3$)$_2$ | N |
| L-6 | OCF$_2$H | N(CH$_3$)$_2$ | N |
| L-7 | NHCH$_3$ | OCH$_3$ | CH |
| L-7 | NHCH$_3$ | CH$_3$ | CH |
| L-7 | NHCH$_3$ | OCH$_2$CF$_3$ | CH |
| L-7 | NHCH$_3$ | OCF$_2$H | CH |
| L-7 | OCH$_3$ | NHCH$_3$ | CH |
| L-7 | CH$_3$ | NHCH$_3$ | CH |
| L-7 | OCH$_2$CF$_3$ | NHCH$_3$ | CH |
| L-7 | OCF$_2$H | NHCH$_3$ | CH |
| L-7 | N(CH$_3$)$_2$ | OCH$_3$ | CH |
| L-7 | N(CH$_3$)$_2$ | CH$_3$ | CH |
| L-7 | N(CH$_3$)$_2$ | OCH$_2$CF$_3$ | CH |
| L-7 | N(CH$_3$)$_2$ | OCF$_2$H | CH |
| L-7 | OCH$_3$ | N(CH$_3$)$_2$ | CH |
| L-7 | CH$_3$ | N(CH$_3$)$_2$ | CH |
| L-7 | OCH$_2$CF$_3$ | N(CH$_3$)$_2$ | CH |
| L-7 | OCF$_2$H | N(CH$_3$)$_2$ | CH |
| L-7 | OCH$_3$ | OCH$_3$ | CH |
| L-7 | OCH$_3$ | CH$_3$ | CH |
| L-7 | CH$_3$ | OCH$_3$ | CH |
| L-7 | CH$_3$ | CH$_3$ | CH |
| L-7 | CH$_3$ | Cl | CH |
| L-7 | Cl | CH$_3$ | CH |
| L-7 | Cl | OCH$_3$ | CH |
| L-7 | OCH$_3$ | Cl | CH |
| L-7 | OCH$_3$ | OCH$_3$ | N |
| L-7 | OCH$_3$ | CH$_3$ | N |
| L-7 | CH$_3$ | OCH$_3$ | N |
| L-7 | CH$_3$ | CH$_3$ | N |
| L-7 | CH$_3$ | Cl | N |
| L-7 | Cl | CH$_3$ | N |
| L-7 | Cl | OCH$_3$ | N |
| L-7 | OCH$_3$ | Cl | N |
| L-7 | NHCH$_3$ | OCH$_3$ | N |
| L-7 | NHCH$_3$ | CH$_3$ | N |
| L-7 | NHCH$_3$ | OCH$_2$CF$_3$ | N |
| L-7 | NHCH$_3$ | OCF$_2$H | N |
| L-7 | OCH$_3$ | NHCH$_3$ | N |
| L-7 | CH$_3$ | NHCH$_3$ | N |
| L-7 | OCH$_2$CF$_3$ | NHCH$_3$ | N |
| L-7 | OCF$_2$H | NHCH$_3$ | N |
| L-7 | N(CH$_3$)$_2$ | OCH$_3$ | N |
| L-7 | N(CH$_3$)$_2$ | CH$_3$ | N |
| L-7 | N(CH$_3$)$_2$ | OCH$_2$CF$_3$ | N |
| L-7 | N(CH$_3$)$_2$ | OCF$_2$H | N |

TABLE 1-continued

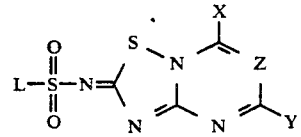

| L | X | Y | Z |
|---|---|---|---|
| L-7 | OCH$_3$ | N(CH$_3$)$_2$ | N |
| L-7 | CH$_3$ | N(CH$_3$)$_2$ | N |
| L-7 | OCH$_2$CF$_3$ | N(CH$_3$)$_2$ | N |
| L-7 | OCF$_2$H | N(CH$_3$)$_2$ | N |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 5

|  | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., N.Y., 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, N.Y., 1973, pp. 8-57ff.

In the following examples, all parts are by weight unless otherwise indicated.

EXAMPLE 3

| Wettable Powder | |
|---|---|
| N-(5,7-dimethoxy-2H-[1,2,4]thiadiazolo[2,3-a]-pyrimidin-2-ylidene)-3-(ethylsulfonyl)-2-pyridinesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 50 microns in diameter. The product is reblended before packaging.

EXAMPLE 4

| Granule | |
|---|---|
| Wettable Powder of Example 3 | 5% |
| attapulgite granules (U.S.S. 20-40 mesh; 0.84-0.42 mm) | 95% |

A slurry of wettable powder containing 25% solids is sprayed on the surface of attapulgite granules in a double-cone blender. The granules are dried and packaged.

EXAMPLE 5

| Extruded Pellet | |
|---|---|
| N-(5,7-dimethoxy-2H-[1,2,4]thiadiazolo[2,3-a]-pyrimidin-2-ylidene)-1-methyl-4-(2-methyl-2H-tetrazol-5-yl)-1H-pyrazole-5-sulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 6

| Low Strength Granule | |
|---|---|
| N-(5,7-dimethoxy-2H-[1,2,4]thiadiazolo[2,3-a]-pyrimidin-2-ylidene)-3-(ethylsulfonyl)-2-pyridinesulfonamide | 1% |
| N,N-dimethylformamide | 9% |
| attapulgite granules (U.S.S. 20–40 sieve, 0.42 to 0.84 mm) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 7

| Aqueous Suspension | |
|---|---|
| N-(5,7-dimethoxy-2H-[1,2,4]thiadiazolo[2,3-a]-pyrimidin-2-ylidene)-1-methyl-4-(2-methyl-2H-tetrazol-5-yl)-1H-pyrazole-5-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 8

| Oil Suspension | |
|---|---|
| N-(5,7-dimethoxy-2H-[1,2,4]thiadiazolo[2,3-a]-pyrimidin-2-ylidene)-3-(ethylsulfonyl)-2-pyridinesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 9

| Granule | |
|---|---|
| N-(5,7-dimethoxy-2H-[1,2,4]thiadiazolo[2,3-a]-pyrimidin-2-ylidene)-1-methyl-4-(2-methyl-2H-tetrazol-5-yl)-1H-pyrazole-5-sulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh (149 microns) screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 10

| High Strength Concentrate | |
|---|---|
| N-(5,7-dimethoxy-2H-[1,2,4]thiadiazolo[2,3-a]-pyrimidin-2-ylidene)-3-(ethylsulfonyl)-2-pyridinesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 11

| Wettable Powder | |
|---|---|
| N-(5,7-dimethoxy-2H-[1,2,4]thiadiazolo[2,3-a]-pyrimidin-2-ylidene)-1-methyl-4-(2-methyl-2H-tetrazol-5-yl)-1H-pyrazole-5-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 12

| Wettable Powder | |
|---|---|
| N-(5,7-dimethoxy-2H-[1,2,4]thiadiazolo[2,3-a]-pyrimidin-2-ylidene)-3-(ethylsulfonyl)-2-pyridinesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 13

| Dust | |
|---|---|
| N-(5,7-dimethoxy-2H-[1,2,4]thiadiazolo[2,3-a]-pyrimidin-2-ylidene)-1-methyl-4-(2-methyl-2H-tetrazol-5-yl)-1H-pyrazole-5-sulfonamide | 10% |
| attapulgite | 10% |
| talc | 80% |

The active ingredient is blended with attapulgite and then passed through a hammer-mill to produce particles substantially all below 200 microns. The ground concentrate is then blended with powdered pyrophyllite until homogeneous.

EXAMPLE 14

| Solution | |
|---|---|
| N-(5,7-dimethoxy-2H-[1,2,4]thiadiazolo[2,3-a]-pyrimidin-2-ylidene)-3-(ethylsulfonyl)-2-pyridinesulfonamide, sodium salt | 5% |

-continued

| Solution | |
|---|---|
| water | 95% |

The salt is added directly to the water with stirring to produce the solution, which may then be packaged for use.

EXAMPLE 15

| Solution | |
|---|---|
| N-(5,7-dimethoxy-2H-[1,2,4]thiadiazolo[2,3-a]-pyrimidin-2-ylidene)-1-methyl-4-(2-methyl-2H-tetrazol-5-yl)-1H-pyrazole-5-sulfonamide, sodium salt | 5% |
| water | 95% |

The salt is added directly to the water with stirring to produce the solution, which may then be packaged for use.

UTILITY

Compounds of this invention are useful as postemergence and/or preemergence herbicides for the control of selected grass and broadleaf weeds with tolerance to important agronomic crops such as barley (*Hordeum vulgare*), corn (*Zea mays*), potato (*Solanum tuberosum*), rape (*Brassica napus*), rice (*Oryza sativa*), soybean (*Glycine max*), sugar beet (*Beta vulgaris*), tomato (*Lycopersicon esculentum*) or wheat (*Triticum aestivum*). Utility in rice includes upland rice, direct-seeded paddy rice, or transplanted paddy rice.

Compounds of this invention also have utility in non-crop areas where selected weed control is desired, such as around storage tanks, parking lots, drive-in theaters, billboards, highways, and railroad structures. These compounds are also useful in fallow areas of crop production such as in wheat and barley and in plantation crops such as palm, banana, citrus, rubber, etc. Alternatively, these compounds may be useful to modify plant growth or as citrus abscission agents.

An effective amount of the compounds of the invention are applied at rates of application determined by a number of factors. These factors include: formulation selected, method of application, amount of vegetation present, growing conditions, etc. In general terms, effective amounts of compounds of this invention are applied at rates from 0.01 to 20 kg/ha with a preferred rate range of from 0.02 to 1 kg/ha. One skilled in the art can easily determine rates needed for the desired level of weed control.

Compounds of this invention may be used alone or in combination with other commercial herbicides, insecticides, or fungicides. The following list exemplifies some of the herbicides suitable for use in mixtures. A combination of compounds from this invention with one or more of the following herbicides may be particularly useful for weed control.

| Common Name | Chemical Name |
|---|---|
| acetochlor | 2-chloro-N-(ethoxymethyl)-N-(2-ethyl-6-methylphenyl)acetamide |
| acifluorfen | 5-[2-chloro-4-(trifluoromethyl)-phenoxy]-2-nitrobenzoic acid |
| acrolein | 2-propenal |
| alachlor | 2-chloro-N-(2,6-diethylphenyl)-N-(methoxymethyl)acetamide |

-continued

| Common Name | Chemical Name |
|---|---|
| anilofos | S-4-chloro-N-isopropylcarbaniloyl-methyl-O,O-dimethyl phosphorodithioate |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| asulam | methyl [(4-aminophenyl)sulfonyl]-carbamate |
| atrazine | 6-chloro-N-ethyl-N'-(1-methylethyl)-1,3,5-triazine-2,4-diamine |
| barban | 4-chloro-2-butynyl 3-chlorocarbamate |
| benefin | N-butyl-N-ethyl-2,6-dinitro-4-(trifluoromethyl)benzenamine |
| bensulfuron methyl | 2-[[[[(4,6-dimethoxy-2-pyrimidinyl)amino]methylcarbonyl]-amino]sulfonyl]methyl]benzoic acid, methyl ester |
| bensulide | O,O-bis(1-methylethyl) S-[2-[(phenylsulfonyl)amino]-ethyl]phosphorodithioate |
| bentazon | 3-(1-methylethyl)-(1H)-2,1,3-benzothiadiazin-4(3H)-one, 2,2-dioxide |
| benzofluor | N-[4-(ethylthio)-2-(trifluoromethyl)phenyl]methanesulfonamide |
| benzoylprop | N-benzoyl-N-(3,4-dichlorophenyl)-DL-alanine |
| bifenox | methyl 5-(2,4-dichlorophenoxy)-2-nitrobenzoate |
| bromacil | 5-bromo-6-methyl-3-(1-methylpropyl)-2,4(1H,3H)pyrimidinedione |
| bromoxynil | 3,5-dibromo-4-hydroxybenzonitrile |
| butachlor | N-(butoxymethyl)-2-chloro-N-(2,6-diethylphenyl)acetamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methyl-propyl)-2,6-dinitrobenzenamine |
| butylate | S-ethyl bis(2-methylpropyl)-carbamothioate |
| cacodylic acid | dimethyl arsinic oxide |
| CDAA | 2-chloro-N,N-di-2-propenylacetamide |
| CDEC | 2-chloroallyl diethyldithiocarbamate |
| CGA 142,464 | 3-(4,6-dimethoxy-1,3,5-triazin-2-yl)-1-[2-(2-methoxyethoxy)-phenyl-sulfonyl]-urea |
| chloramben | 3-amino-2,5-dichlorobenzoic acid |
| chlorbromuron | 3-(4-bromo-3-chlorophenyl)-1-methoxy-1-methylurea |
| chlorimuron ethyl | 2-[[[[(4-chloro-6-methoxy-2-pyrimidinyl)ethylamino]carbonyl]-amino]sulfonyl]benzoic acid, ethyl ester |
| chlormethoxynil | 2,4-dichlorophenyl 4-nitro-3-methoxyphenyl ether |
| chlornitrofen | 2,4,6-trichlorophenyl-4-nitro-phenyl ether |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]benzenesulfonamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo-[2.2.1]heptane |
| clethodim | (E,E)-(±)-2-[1-[[(3-chloro-2-propenyl)-oxy]imino]propyl]-5-[2-(ethylthio)-propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy)-imino]butyl]-5-[2-(ethylthio)propyl]-3-hydroxy-2-cyclohexen-1-one |
| clopyralid | 3,6-dichloro-2-pyridinecarboxylic acid |

-continued

| Common Name | Chemical Name |
|---|---|
| CMA | calcium salt of MAA |
| cyanazine | 2-[[4-chloro-6-(ethylamino)-1,3,5-triazin-2-yl]amino]-2-methylpropanenitrile |
| cycloate | S-ethyl cyclohexylethylcarbamothioate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmediphan | ethyl [3-[[(phenylamino)carbonyl]oxy]phenyl]carbamate |
| desmetryn | 2-(isopropylamino)-4-(methylamino)-6-(methylthio)-s-triazine |
| diallate | S-(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (±)-2-(2,4-dichlorophenoxy)propanoic acid |
| dichlofop | (±)-2-[4-(2,4-dichlorophenoxy)phenoxy]propanoic acid, methyl ester |
| diethatyl | N-(chloroacetyl)-N-(2,6-diethylphenyl)glycine |
| difenzoquat | 1,2-dimethyl-3,5-diphenyl-1H-pyrazolium |
| dimepiperate | S-1-methyl-1-phenylethylpiperidine-1-carbothioate |
| dinitramine | N³,N³-diethyl-2,4-dinitro-6-(trifluoromethyl)-1,3-benzenediamine |
| dinoseb | 2-(1-methylpropyl)-4,6-dinitrophenol |
| diphenamid | N,N-dimethyl-α-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]pyrazinedium ion |
| diuron | N'-(3,4-dichlorophenyl)-N,N-dimethylurea |
| DNOC | 2-methyl-4,6-dinitrophenol |
| DPX-M6316 | 3-[[[[(4-methoxy-6-methyl-1,3,5-triazin-2-yl)amino]carbonyl]amino]sulfonyl]-2-thiophenecarboxylic acid, methyl ester |
| DSMA | disodium salt of MAA |
| dymron | N-(4-methylphenyl)-N'-(1-methyl-1-phenylethyl)urea |
| endothall | 7-oxabicyclo[2.2.1]heptane-2,3-dicarboxylic acid |
| EPTC | S-ethyl dipropylcarbamothioate |
| esprocarb (SC2957) | S-benzyl-N-ethyl-N-(1,2-dimethyl)propyl)thiolcarbamate |
| ethalfluralin | N-ethyl-N-(2-methyl-2-propenyl)-2,6-dinitro-4-(trifluoromethyl)benzenamine |
| ethofumesate | (±)-2-ethoxy-2,3-dihydro-3,3-dimethyl-5-benzofuranyl methanesulfonate |
| Express ® | 2-[[[[N-(4-methoxy-6-methyl-1,3,5-triazine-2-yl)-N-methylamino]carbonyl]amino]sulfonyl]benzoic acid, methyl ester |
| fenac | 2,3,6-trichlorobenzeneacetic acid |
| fenoxaprop | (±)-2-[4-[(6-chloro-2-benzoxazolyl)oxy]phenoxy]propanoic acid |
| fenuron | N,N-dimethyl-N'-phenylurea |
| fenuron TCA | Salt of fenuron and TCA |
| flamprop | N-benzoyl-N-(3-chloro-4-fluorophenyl)-DL-alanine |
| fluazifop | (±)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chloroethyl)-2,6-dinitro-N-propyl-4-(trifluoromethyl)benzenamine |
| fluometuron | N,N-dimethyl-N'-[3-(trifluoromethyl)phenyl]urea |
| fluorochloridone | 3-chloro-4-(chloromethyl)-1-[3-(trifluoromethyl)phenyl]-2-pyrrolidinone |
| fluorodifen | p-nitrophenyl α,α,α-trifluoro-2-nitro-p-tolyl ether |
| fluoroglycofen | carboxymethyl 5-[2-chloro 4-(trifluoromethyl)phenoxy]-2-nitrobenzoate |
| fluridone | 1-methyl-3-phenyl-5-[3-(trifluoromethyl)phenyl]-4(1H)-pyridinone |
| fomesafen | 5-[2-chloro-4-(trifluoromethyl)phenoxy]-N-(methylsulfonyl)-2-nitrobenzamide |
| fosamine | ethyl hydrogen (aminocarbonyl)phosphate |
| glyphosate | N-(phosphonomethyl)glycine |
| haloxyfop | 2-[4-[[3-chloro-5-(trifluoromethyl)-2-pyridinyl]oxy]phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)-dione |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (±)-2-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | (±)-2-[4,5-dihydro-4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isopropalin | 4-(1-methylethyl)-2,6-dinitro-N,N-dipropylbenzenamine |
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]phenyl-(1,1-dimethylethyl)carbamate |
| lactofen | (+)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopenta-pyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| MON 7200 | S,S-dimethyl-2-(difluoromethyl)-4-(2-methylpropyl)-6-(trifluoromethyl)-3,5-pyridinedicarbothionate |
| mecoprop | (±)-2-(4-chloro-2-methylphenoxy)propanoic acid |
| mefenacet | 2-(2-benzothiazolyloxy-N-methyl-N-phenylacetamide |
| mefluidide | N-[2,4-dimethyl-5-[[(trifluoromethyl)sulfonyl]amino]phenyl]acetamide |
| methalpropalin | N-(2-methyl-2-propenyl)-2,6-dinitro-N-propyl-4-(trifluoromethyl)benzenamide |
| methabenzthiazuron | 1,3-dimethyl-3-(2-benzothiazolyl)urea |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| metolachlor | 2-chloro-N-(2-ethyl-6-methylphenyl)-N-(2-methoxy-1-methylethyl)acetamide |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)amino]carbonyl]amino]sulfonyl]benzoic acid, methyl ester |
| MH | 1,2-dihydro-3,6-pyridazinedione |
| molinate | S-ethyl hexahydro-1H-azepine-1-carbo- |

-continued

| Common Name | Chemical Name |
|---|---|
| monolinuron | 3-(p-chlorophenyl)-1-methoxy-1-methylurea |
| monuron | N'-(4-chlorophenyl)-N,N-dimethylurea |
| monuron TCA | Salt of monuron and TCA |
| MSMA | monosodium salt of MAA |
| napropamide | N,N-diethyl-2-(1-naphthalenyloxy)-propanamide |
| naptalam | 2-[(1-naphthalenylamino)carbonyl]-benzoic acid |
| neburon | 1-butyl-3-(3,4-dichlorophenyl)-1-methylurea |
| nitralin | 4-(methylsulfonyl)-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3aα,-4α,5α,7α,7aα-isomer |
| norflurazon | 4-chloro-5-(methylamino)-2-[3-(trifluoromethyl)phenyl]-3(2H)-pyridazinone |
| oryzalin | 4-(dipropylamino)-3,5-dinitro-benzenesulfonamide |
| oxadiazon | 3-[2,4-dichloro-5-(1-methylethoxy)phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| phenmedipham | 3-[(methoxycarbonyl)amino]phenyl (3-methylphenyl)carbamate |
| picloram | 4-amino-3,5,6-trichloro-2-pyridine-carboxylic acid |
| PPG-1013 | 5-[2-chloro-4-(trifluoromethyl)phenoxy]-2-nitroacetophenone oxime-O-acetic acid, methyl ester |
| pretilachlor | α-chloro-2,6-diethyl-N-(2-propoxyethyl)acetanilide |
| procyazine | 2-[[4-chloro-6-(cyclopropylamino)-1,3,5-triazine-2-yl]amino]-2-methylpropanenitrile |
| profluralin | N-(cyclopropylmethyl)-2,6-dinitro-N-propyl-4-(trifluoromethyl)benzenamine |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenylacetamide |
| propanil | N-(3,4-dichlorophenyl)propanamide |
| propazine | 6-chloro-N,N'-bis(1-methylethyl)-1,3,5-triazine-2,4-diamine |
| propham | 1-methylethyl phenylcarbamate |
| prosulfalin | N-[[4-(dipropylamino)-3,5-dinitrophenyl]sulfonyl]-S,S-dimethylsulfilimine |
| prynachlor | 2-chloro-N-(1-methyl-2-propynyl)acetanilide |
| pyrazolate | 4-(2,4-dichlorobenzoyl)-1,3-dimethylpyrazol-5-yl-p-toluenesulphonate |
| pyrazon | 5-amino-4-chloro-2-phenyl-3(2H)-pyridazinone |
| pyrazosulfuron ethyl | ethyl 5-[3-(4,6-dimethoxypyrimidin-2-yl)ureadosulfonyl]-1-methylpyrazole-4-carboxylate |
| quinclorac | 3,7-dichloro-8-quinoline carboxylic acid |
| quizalofop ethyl | (±)-2-[4-[(6-chloro-2-quinoxalinyl)oxy]phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethyl- |

-continued

| Common Name | Chemical Name |
|---|---|
| | thio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| SK-233 | 1-(α,α-dimethylbenzyl)-3-(4-methylphenyl)urea |
| sulfometuron methyl | 2-[[[[(4,6-dimethyl-2-pyrimidinyl)-amino]carbonyl]amino]sulfonyl]-benzoic acid, methyl ester |
| TCA | trichloroacetic acid |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]-acetamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thiobencarb | S-[(4-chlorophenyl)methyl]diethylcarbamothioate |
| triallate | S-(2,3,3-trichloro-2-propenyl)bis(1-methylethyl)carbamothioate |
| triclopyr | [(3,5,6-trichloro-2-pyridinyl)-oxy]acetic acid |
| tridiphane | 2-(3,5-dichlorophenyl)-2-(2,2,2-trichloroethyl)oxirane |
| trifluralin | 2,6-dinitro-N,N-dipropyl-4-(trifluoromethyl)benzenamine |
| trimeturon | 1-(p-chlorophenyl)-2,3,3-trimethylpseudourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

COMPOUND TABLE

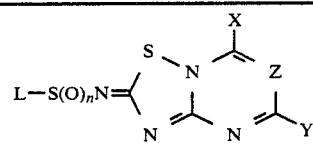

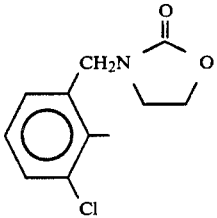 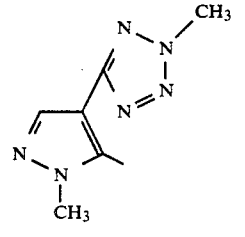

L-3      L-6

| Compound | L | X | Y | Z | m.p. °C. |
|---|---|---|---|---|---|
| 1 | L-3 | OCH$_3$ | OCH$_3$ | CH | 141–142 |
| 2 | L-6 | OCH$_3$ | OCH$_3$ | CH | 182–183 |

What is claimed is:
1. Compounds of Formula I,

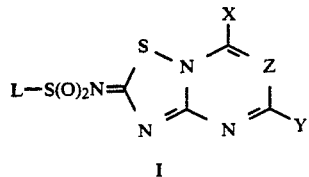

wherein

L is

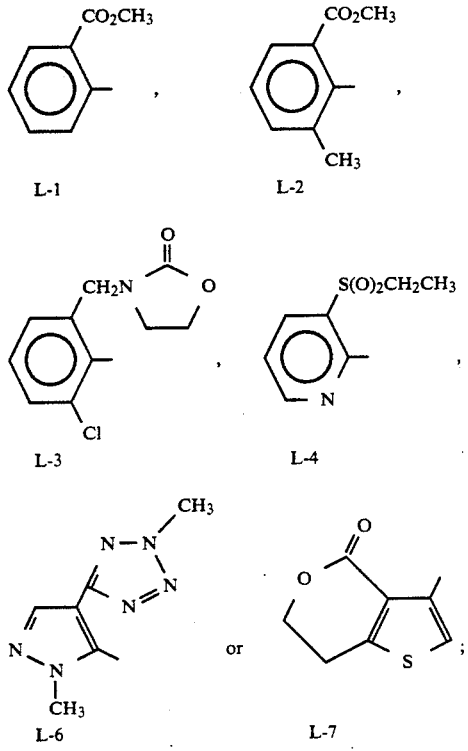

X and Y are independently $C_1$-$C_2$ alkyl, $C_1$-$C_2$ alkoxy, $C_1$-$C_2$ haloalkoxy, NHCH$_3$ or N(CH$_3$)$_2$; and Z is CH; and their agriculturally suitable salts provided that 1) when X and/or Y is $C_1$ haloalkoxy, then Z is CH; and 2) when L is L-1 or L-2, then at least one of X and Y is NHCH$_3$ or N(CH$_3$)$_2$.

2. Compounds of claim 1 where X and Y are independently $C_1$-$C_2$ alkyl, $C_1$-$C_2$ alkoxy, OCF$_2$H or OCH$_2$CF$_3$, or one of X and Y can be NHCH$_3$ or N(CH$_3$)$_2$.

3. Compounds of claim 2 where X and Y are independently CH$_3$ or OCH$_3$.

4. The compound of claim 1 which is N-(5,7-dimethoxy-2H-[1,2,4]thiadiazolo[2,3-a]pyrimidin-2-ylidene)-3-(ethylsulfonyl)-2-pyridinesulfonamide.

5. The compound of claim 1 which is N-(5,7-dimethoxy-2H-[1,2,4]thiadiazolo[2,3-a]pyrimidin-2-ylidene)-1-methyl-4-(2-methyl-1H-tetrazol-5-yl)-1H-pyrazole-5-sulfonamide.

6. An agriculturally suitable composition for controlling the growth of undesired vegetation comprising an effective amount of the compound of claim 1 and at least one of the following: surfactant, solid diluent or liquid diluent.

7. An agriculturally suitable composition for controlling the growth of undesired vegetation comprising an effective amount of the compound of claim 2 and at least one of the following: surfactant, solid diluent or liquid diluent.

8. An agriculturally suitable composition for controlling the growth of undesired vegetation comprising an effective amount of the compound of claim 3 and at least one of the following: surfactant, solid diluent or liquid diluent.

9. An agriculturally suitable composition for controlling the growth of undesired vegetation comprising an effective amount of the compound of claim 4 and at least one of the following: surfactant, solid diluent or liquid diluent.

10. An agriculturally suitable composition for controlling the growth of undesired vegetation comprising an effective amount of the compound of claim 5 and at least one of the following: surfactant, solid diluent or liquid diluent.

11. A method for controlling the growth of undesired vegetation which comprises applying to the locus to be protected an effective amount of a compound of claim 1.

12. A method for controlling the growth of undesired vegetation which comprises applying to the locus to be protected an effective amount of a compound of claim 2.

13. A method for controlling the growth of undesired vegetation which comprises applying to the locus to be protected an effective amount of a compound of claim 3.

14. A method for controlling the growth of undesired vegetation which comprises applying to the locus to be protected an effective amount of a compound of claim 4.

15. A method for controlling the growth of undesired vegetation which comprises applying to the locus to be protected an effective amount of a compound of claim 5.

* * * * *